United States Patent [19]

Emmer et al.

[11] Patent Number: 4,765,870

[45] Date of Patent: Aug. 23, 1988

[54] METHOD OF MANUFACTURE OF AN ELECTRIC MOISTURE-CONTENT SENSOR

[75] Inventors: Ivan Emmer; Zdeněk Hájek; Petr Řepa, all of Prague, Czechoslovakia

[73] Assignee: Matematicko-Fyzikalni Fakulta University, Prague, Czechoslovakia

[21] Appl. No.: 47,805

[22] Filed: May 8, 1987

[51] Int. Cl.$^4$ .................. C25F 3/20; C23C 14/16; C23C 14/34; C23C 22/56

[52] U.S. Cl. .................. 204/129.1; 204/192.15; 204/192.22; 204/192.23; 148/6.27; 156/665; 427/343; 427/419.2

[58] Field of Search .................. 148/6.15 R, 6.27; 204/129.3, 33, 192.15, 192.22, 192.23, 129.1; 156/665; 427/343, 419.2

[56] References Cited

U.S. PATENT DOCUMENTS

| | | | |
|---|---|---|---|
| 3,574,681 | 4/1971 | Cecil | 148/6.27 X |
| 3,900,370 | 8/1975 | Germscheid et al. | 148/6.27 X |
| 4,144,636 | 3/1979 | Burkhardt et al. | 204/129.3 X |
| 4,204,919 | 5/1980 | Randall, Jr. et al. | 204/33 X |
| 4,470,885 | 9/1984 | Randall, Jr. et al. | 204/33 X |

Primary Examiner—Donald R. Valentine
Attorney, Agent, or Firm—Klein & Vibber

[57] ABSTRACT

The present invention relates to a method of manufacture of an electric moisture-content sensor comprising a porous layer of alumuniumoxihydroxide, the so-called boehmite, obtained by hydration of an aluminium substrate in boiling redistilled water and subsequent passivating tempering.

This method, due to its simplicity, results in a larger yield in manufacture, reduced variations of parameters of individual sensors and a higher stability of their calibration curves.

Due to the extraordinary prolonged stability of sensors manufactured according to this method, they can be for example applied for measuring of the moisture content of stored goods, for air-conditioning systems, for drying plants, in meteorology and also for microelectronics and in medicine.

6 Claims, 1 Drawing Sheet

METHOD OF MANUFACTURE OF AN ELECTRIC MOISTURE-CONTENT SENSOR

FIELD OF THE INVENTION

The invention relates to a method of manufacture of a moisture-content sensor.

BACKGROUND OF THE INVENTION

One method for measuring the moisture content of a medium is by application of sensors, by means of which the moisture content is expressed by an electric signal. At present, known sensors for measuring moisture content are made with lithium chloride which is applied with a suitable binding agent on a support. Other known sensors are made with powder carbon, with layers of different polymers or manufactured on the basis of porous aluminium oxide.

Sensors with lithium chloride and with powder carbon and with polymers are sensitive to moisture due to variations of their volume in different layers. Their drawback is however a long reaction time to changes of moisture, the instability of their calibration curve and their high dependence on the temperature of the sensor.

A sensor with a thin porous layer of aluminium oxide where water is absorbed on the surface of pores of its layer causing thereby a change of electric parameters of the sensor, offers more advantageous properties. In this case surface layers are concerned and the reaction time is substantially shortened. The prolonged calibration stability which can be achieved and the resulting value of electric impedance of these sensors depend on the technology which has been applied for preparation of the layer of aluminium oxide and on its further treatment.

Good results have been obtained with sensors manufactured according to U.S. Pat. No. 3,075,385 where the porous layer of aluminium oxide is formed on the surface of a clean, polished aluminium sheet which forms simultaneously a main electrode of the sensor, by anodic oxidation by alternating current having a density of about 13 mA/cm$^2$ in 50% sulphuric acid at a temperature of 33 degrees C. for 35 minutes. The thus obtained layer of a thickness of 2 $\mu$m is, just after rinsing with distilled water, exposed to a hydratation in boiling redistilled water, to the so-called sealing, which proceeds for about 30 minutes. The surface of the porous aluminium oxide is covered in the course of this process by a thin layer of aluminiumoxihydroxide, by the so-called boehmite. A thin semipervious counter electrode is created by a suitable method on a part of the thus prepared composite layer. The obtained condensor structure reacts to a change of the surrounding moisture by a change of electric parameters, which changes are evaluated. Sensors manufactured acording to this process are sensitive within a wide range of moisture content and have a relatively short reaction time, their drawback is however that, due to absorption of water to the porous layer, a further consecutive hydratation is caused leading to non-recurring changes of the structure of the sensor and to a reduction of its sensitivity.

A process described in U.S. Pat. No. 3,523,244, which is a modification of the above-mentioned process, uses a layer of aluminium oxide, the thickness of which is, after hydratation, reduced by mechanical grinding to about 300 nm, due to which reduction a reduction of the reaction time in the sensor is achieved.

The above-mentioned drawbacks are much reduced by a manufacturing method described in Czechoslovak certificates of authorship of inventions No. 197 742 and 210 174 and in U.S. Pat. No. 4,441,968, where the surface of aluminium oxide is, prior to application of a counter electrode, passivated for instance by soaking in an aqueous solution of 0.1 mol/liter sodium-hydrogenphosphate at 90 degrees C. for a time of 10 minutes with a following tempering in a gaseous medium which is chemically inert against the thus created layer at a temperature of 90 degrees C. for 8 hours. It is suitable if this medium contains water vapors of a lower pressure than the aqueous water tension at the tempering temperature.

Although the thus prepared sensor has a very good calibration stability, its drawback is that its manufacturing process is rather complicated as it contains a number of different operations. That leads generally to a more frequent occurrence of faulty products, to a dissipation of resulting parameters of individual sensors and to certain variations of the shape of their calibration curves.

It is an object of this invention to provide a method of manufacturing an electric moisture-content sensor which eliminates or reduces the above mentioned drawbacks.

SUMMARY OF THE INVENTION

The method of manufacturing electric moisture-content sensors according to this invention provides that a layer of alumuniumoxihydroxide be created on a clean aluminium substrate by its hydratation in boiling redistilled water for a time of 5 to 60 minutes, which layer is passivated by soaking in an aqueous solution of sodium dihydrogenphosphate of a concentration of 0.01 to 2 mol/liter at a temperature of 35 to 100 degrees C. for 5 to 60 minutes.

A clean aluminium substrate can be provided by compact aluminium advantageously in the shape of a sheet polished chemically or electrochemically.

According to an alternative embodiment of the invention, the clean aluminium substrate can be provided by a thin aluminium layer formed for instance by vacuum evaporation coating or sputtering on a support formed by silicon covered by an insulating layer of silicon dioxide.

The passivated layer of aluminiumoxihydroxide can be subsequently tempered in a gaseous medium which is inert to this layer, advantageously in air at a temperature of 70 to 110 degrees C., for 2 to 24 hours, whereby the medium contains water vapor of a lower pressure than the water vapor tension at the tempering temperature.

An advantage of this process is a simple manufacturing method of an electric moisture-content sensor on the basis of aluminiumdehydroxide leading to a further improvement of the time stability of the calibration curve and of its course. A substantial feature of the manufacturing method acording to this invention is its extraordinary simplicity which advantageously influences the yield and manufacturing costs and leads to a smaller dissipation of parameters of individual sensors.

Another advantage of the method according to this invention is that the active layer of the sensor achieves, when suitable conditions in the course of its manufacture have been selected, a thickness around 300 nm, which proved to be the optimum in order to obtain a short reaction time.

Another advantage of this manufacturing method is that is quite compatible with the technology of forming integrated circuits, enabling not only to provide moisture sensors of fully miniaturized sizes but to use them as parts of integrated circuits.

The sensor manufactured by the method acording to this invention reacts to variations of the absolute moisture of the surrounding medium within an extremely wide range at a very short reaction time, whereby its prolonged time stability is, at a more suitable course of the calibration curve, at least the same or better than with known sensors of this type.

BRIEF DESCRIPTION OF THE DRAWING

With these and other objects in view, which will become apparent in the following detailed description, the present invention, which is shown by example only, will be clearly understood in connection with the accompanying drawing, in which.

DESCRIPTION OF THE PREFERRED EMBODIMENTS

Figure 1:
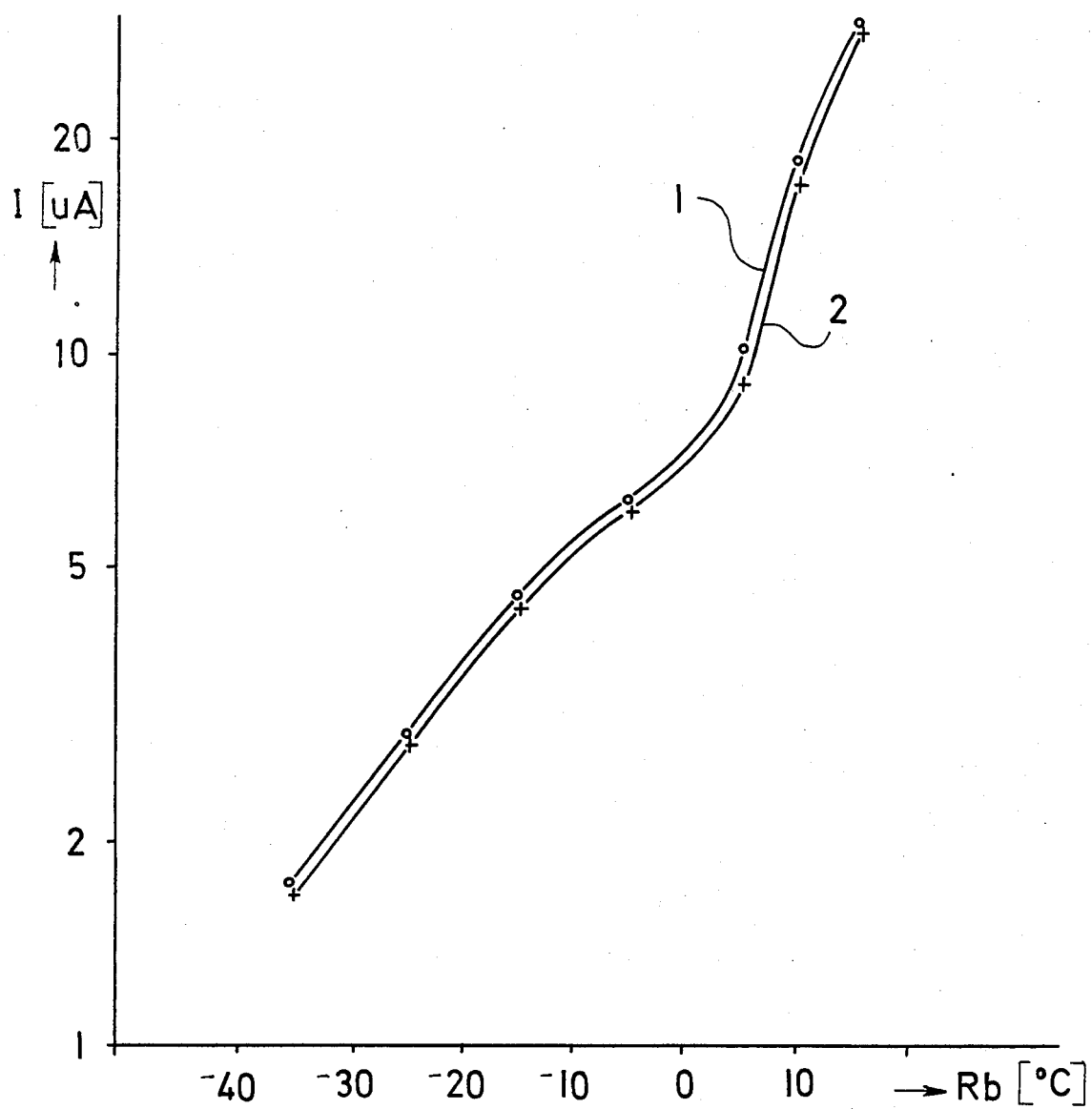
FIG. 1 shows a typical calibration curve and its time stability where Rb is the dew point.

With reference to FIG. 1, the dew point is drawn on the x-axis in degrees C., the current in uA passing through the sensor is drawn on the y-axis. The calibration curve 1 in FIG. 1 shows the dependency of the sensor signal of the sensor manufactured according to this invention on the surrounding moisture-content. The curve 2 in FIG. 1 shows the same dependency determined 6 months later. The mutual distance of both calibration curves is thus a measure of the stability of the sensor.

Figure 2:
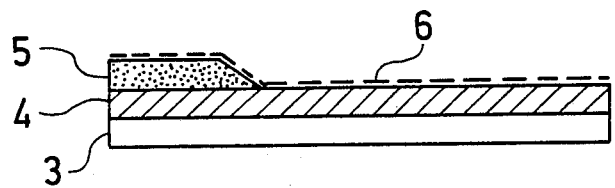
FIG. 2 shows a cross-sectional view of the structure of the sensor manufactured according to the invention.

FIG. 2 shows a cross-sectional view of the sensor which consists solely of a main electrode 3 provided with a layer of boehmite 4, on which a semipervious electrode 6 is deposited. The scope of the separating layer 5 is the same as with known sensors.

The structure of the sensor maunfactured according to this invention is thus simple in manufacture as it contains only a single component layer of boehmite 4 as compared with the composite layer used with known sensors. The main electrode 3 is usually made of a hard drawn aluminium sheet of a purity of 99.99% and of a thickness of 0.25 mm. It is also possible to use materials of lower purity and of different thickness. The semipervious counter electrode 6 is formed as a vacuum evaporated coating of gold of a thickness around 100 nm. Other materials such as platinum, nickel or aluminium can also be used.

EXAMPLE 1

On an aluminium sheet having a thickness of 0.25 mm and of a purity of 99.99%, the surface of which has been treated by chemical or electrochemical polishing, a layer of boehmite is created by direct hydratation in boiling redistilled water for 30 minutes. Immediately after the hydratation this layer is passivated by soaking in an aqueous solution of 0.1 mol/liter sodium dihydrogenphosphate at 90 degrees C. for 10 minutes with a following tempering at 90 degrees C. for 8 hours in an air atmosphere saturated by water vapors to 50% of relative humidity. The manufacture of the sensor is finished by application of a separating layer for instance of epoxy resin at the place of the future connection to the counter electrode and by vacuum evaporation of a semipervious golden counter electrode.

EXAMPLE 2

On a silicon support covered by an insulating layer of $SiO^2$ a layer of pure aluminium having a thickness of at least 1 $\mu$m is formed for instance by vacuum evaporating or sputtering. This layer is exposed to hydratation, passivation and tempering as in example 1. Contrary to example 1, however, it is not necessary to provide a separating layer at the place of connection to the counter electrode as it is in this case possible to apply the counter electrode over a suitably shaped mask so that the contact can be formed on the silicon support beyond the active surface of the sensor.

What is claimed is:

1. A method of manufacturing an electric moisture-content sensor comprising the steps of
   on a pure aluminium substrate, creating a layer of aluminiumoxihydroxide by hydratation in boiling redistilled water for 5 to 60 minutes, and
   passivating said layer by soaking in an aqueous solution of sodium dihydrogenphosphate of a concentration of 0.01 to 2 mol/liter at a temperature of 35 to 100 degrees C. for a time of 5 to 60 minutes;
   where the passivated layer of aluminiumoxihydroxide is tempered in a gaseous medium which is chemically inert to said layer, at a temperature between 70 to 110 degrees C. for 2 to 24 hours, said medium containing water vapors of a lower pressure than the tension of water vapors at the tempering temperature.

2. The method as claimed in claim 1, where the pure aluminium substrate is a compact aluminium, polished sheet.

3. The method as claimed in claim 2, where the polished sheet is electrochemically polished.

4. The method as claimed in claim 2, where the polished sheet is chemically polished.

5. The method as claimed in claim 1, where the pure aluminium substrate is formed as a thin layer of aluminium, by vacuum evaporation on a support of silicon covered by an insulating layer of silicon dioxide.

6. The method as claimed in claim 1, where the pure aluminium substrate is formed as a thin layer of aluminium, by sputtering on a support of silicon covered by an insulating layer of silicon dioxide.

* * * * *